United States Patent
Woo et al.

(10) Patent No.: US 7,079,237 B2
(45) Date of Patent: Jul. 18, 2006

(54) APPARATUS FOR INSPECTING A WAFER

(75) Inventors: Jai-Young Woo, Yongin (KR);
Kyung-Ho Kim, Yongin (KR);
Yun-Chang Choi, Osan (KR);
Hye-Jung Choi, Incheon (KR);
Sung-Uk Park, Suwon (KR)

(73) Assignee: Samsung Electronics Co., Ltd., Suwon (KR)

( * ) Notice: Subject to any disclaimer, the term of this patent is extended or adjusted under 35 U.S.C. 154(b) by 449 days.

(21) Appl. No.: 10/680,342

(22) Filed: Oct. 8, 2003

(65) Prior Publication Data

US 2004/0095575 A1    May 20, 2004

(30) Foreign Application Priority Data

Nov. 19, 2002  (KR) ...................... 10-2002-0072039

(51) Int. Cl.
*G01N 21/88* (2006.01)

(52) U.S. Cl. .................................. 356/237.2

(58) Field of Classification Search .. 356/237.2–237.5; 382/145, 149
See application file for complete search history.

(56) References Cited

U.S. PATENT DOCUMENTS

| 6,947,588 | B1 * | 9/2005 | Sim .......................... 382/149 |
| 2005/0023491 | A1 * | 2/2005 | Young et al. .......... 250/559.42 |

FOREIGN PATENT DOCUMENTS

| KR | 2002-026088 | 1/2002 |
| KR | 10-2002-0074014 | 9/2002 |

* cited by examiner

*Primary Examiner*—Richard A. Rosenberger
(74) *Attorney, Agent, or Firm*—Lee & Morse, P.C.

(57) ABSTRACT

An apparatus for inspecting a wafer includes a handling unit for supporting, rotating and moving the wafer in horizontal and vertical directions, a first image acquisition unit for acquiring a first image corresponding to an upper surface of the wafer supported by the handling unit, a second image acquisition unit for acquiring a second image, a third image and a fourth image corresponding to a peripheral portion of the upper surface, a side surface and a lower surface of the wafer supported by the handling unit, respectively, a first driving unit for rotating the second image acquisition unit about a peripheral portion of the wafer supported by the handling unit in order to acquiring the second, third and fourth images, and an image processing unit for inspecting defects of the wafer supported by the handling unit from the first to fourth images.

33 Claims, 10 Drawing Sheets

APPARATUS FOR INSPECTING A WAFER

BACKGROUND OF THE INVENTION

1. Field of the Invention

The present invention relates to an apparatus for inspecting a wafer. More particularly, the present invention relates to an apparatus for inspecting defects of a wafer using images acquired by a charge coupled device (CCD) camera.

2. Description of the Related Art

Generally, semiconductor devices are manufactured through a three-step process. First, a fabricating process is performed to form an electrical device, such as a transistor and a capacitor, on a silicon wafer used as a semiconductor substrate. Second, an inspecting process is performed to inspect electrical characteristics of the semiconductor devices formed on the semiconductor substrate. Third, a packaging process is performed to package the semiconductor devices to protect the semiconductor devices and to enable the installation of the semiconductor devices in the various information communication devices.

The fabricating process typically includes a film deposition process for forming a specific film on the wafer, a chemical and mechanical polishing (CMP) process for planarizing a surface of the film, a photolithography process for forming photoresist patterns on the film, an etching process for forming the film into patterns having the electrical characteristics using the photoresist patterns, an ion implantation process for implanting specific ions into specific portions of the film, a cleaning process for removing impurities remaining on the wafer, an inspection process for inspecting defects of the film and patterns formed on the wafer, or other similar processes.

Recently, causes of defects have become more varied as diameters of wafers have increased and a degree of integration of the semiconductor device has increased. Accordingly, the inspection process has become more important to determine the causes of the defects and to cope effectively with the defects.

An optical microscope or an electron microscope may be employed for the inspection process. Examples of an optical microscope include a charge coupled device (CCD) camera having a light source for illuminating a surface of the wafer, a lens with a high magnifying power, and a CCD memory for converting an image magnified by the lens into image data and for memorizing the image data. Examples of an electron microscope include a scanning electron microscope, a transmission electron microscope, and the like.

The inspection process is generally performed using an optical microscope because an inspection process using an electron microscope requires a relatively long inspection time and is difficult to inspect side and back surfaces of the wafer. A conventional inspection apparatus using an optical microscope inspects only a front surface of the wafer and is not able to inspect the side and back surfaces of the wafer. Therefore, a conventional inspection process on the wafer requires a plurality of inspection apparatuses thereby increasing the cost related to equipment investment and repair work and deteriorating the productivity of the semiconductor device.

Various attempts have been made to solve the foregoing problems. For example, an apparatus for inspecting all surfaces of the wafer has been developed. In operation, the developed apparatus tilts the wafer to inspect the side and back surface of the wafer. However, the developed apparatus is not able to cope effectively with increasing larger wafer diameters, because it is difficult to stably tilt a wafer having a diameter of 300 mm.

SUMMARY OF THE INVENTION

According to an exemplary embodiment of the present invention, an apparatus for inspecting a wafer may be provided that is able to inspect all surfaces, i.e., front, back and side, of a wafer.

According to an exemplary embodiment of the present invention, an apparatus for inspecting a wafer includes a handling unit for supporting, rotating and moving the wafer in horizontal and vertical directions, a first image acquisition unit for acquiring a first image corresponding to an upper surface of the wafer supported by the handling unit, a second image acquisition unit for acquiring a second image, a third image and a fourth image corresponding to a peripheral portion of the upper surface, a side surface and a lower surface of the wafer supported by the handling unit, respectively, a first driving unit for rotating the second image acquisition unit about a peripheral portion of the wafer supported by the handling unit in order to acquiring the second, third and fourth images, and an image processing unit for inspecting defects of the wafer supported by the handling unit from the first to fourth images.

Preferably, the handling unit includes a chuck for supporting the wafer, a second driving unit, connected to the chuck, for rotating the chuck and the wafer, a third driving unit, connected to the second driving unit, for moving the chuck and the second driving unit vertically, a first plate for supporting the third driving unit, and a fourth driving unit, connected to a lower surface of the first plate, for moving the chuck, the second driving unit and the third driving unit horizontally.

The handling unit may further include a second plate having an opening, the chuck and the second driving unit moving in the vertical direction through the opening, a plurality of supporting shafts extending from an upper surface of the plate in the vertical direction in order to support the second plate, and a plurality of supporting pins disposed on an upper surface of the second plate for supporting the wafer while the chuck is placed at a position lower than those of the plurality of supporting pins.

The apparatus for inspecting a wafer may further include a plurality of alignment pins, movably installed in the horizontal direction at peripheral portions of the second plate, for simultaneously moving the wafer supported by the chuck towards the chuck to align a center of the wafer with a central axis of the chuck.

Preferably, the first driving unit includes a motor for providing a driving force to rotate the second image acquisition unit and a supporting arm connected to the motor to support the second image acquisition unit so that the second image acquisition unit is placed near the peripheral portion of the wafer supported by the handling unit.

In an embodiment of the present invention, the apparatus may include an inspection chamber for performing a process for inspecting defects of the wafer supported by handling unit, a load chamber connected to the inspection chamber for loading and unloading the wafer, a transfer robot disposed in the load chamber for transferring the wafer between a container for receiving a plurality of wafers and the inspection chamber, and a stage connected to the load chamber for supporting the container.

In an embodiment of the present invention, the apparatus may further include a base plate for supporting the handling unit, the first image acquisition unit, the second image acquisition and the driving unit, and a vibration control unit for supporting the base plate and for controlling a vibration.

According to another embodiment of the present invention, an apparatus for inspecting a wafer includes a chuck for supporting a wafer and for holding the wafer using a vacuum force, a first driving unit connected to a lower surface of the chuck for rotating the wafer held by the chuck, a three-axis Cartesian coordinate robot for moving the wafer held by the chuck in horizontal and vertical directions, a first image acquisition unit for acquiring a first image corresponding to an upper surface of the wafer held by the chuck, a second image acquisition unit for acquiring a second image, a third image and a fourth image corresponding to a peripheral portion of the upper surface, a side surface and a lower surface of the wafer held by the chuck, respectively, a second driving unit for rotating the second image acquisition unit about a peripheral portion of the wafer held by the chuck in order to acquiring the second, third and fourth images, a supporting arm for supporting the second image acquisition unit and for connecting the second image acquisition unit and the second driving unit so that the second image acquisition unit is placed towards the peripheral portion of the wafer held by the chuck, and an image processing unit for inspecting defects of the wafer held by the chuck from the first to fourth images.

An inspection process incorporating the apparatus according to an embodiment of the present invention simplifies inspection of all surfaces of a wafer, i.e., upper, side, and lower, and reduces the time required for the inspection process. Furthermore, a likelihood of damaging a wafer is reduced because the handling unit supports the wafer in the horizontal direction and the inspecting apparatus may move around the wafer to facilitate inspection of a wafer having an enlarged diameter, e.g., a 300 mm diameter.

BRIEF DESCRIPTION OF THE DRAWINGS

To provide a more complete understanding of the present invention and the features and advantages thereof, reference is now made to the following descriptions taken in conjunction with the accompanying drawings, in which.

DETAILED DESCRIPTION OF THE INVENTION

Figure 1:
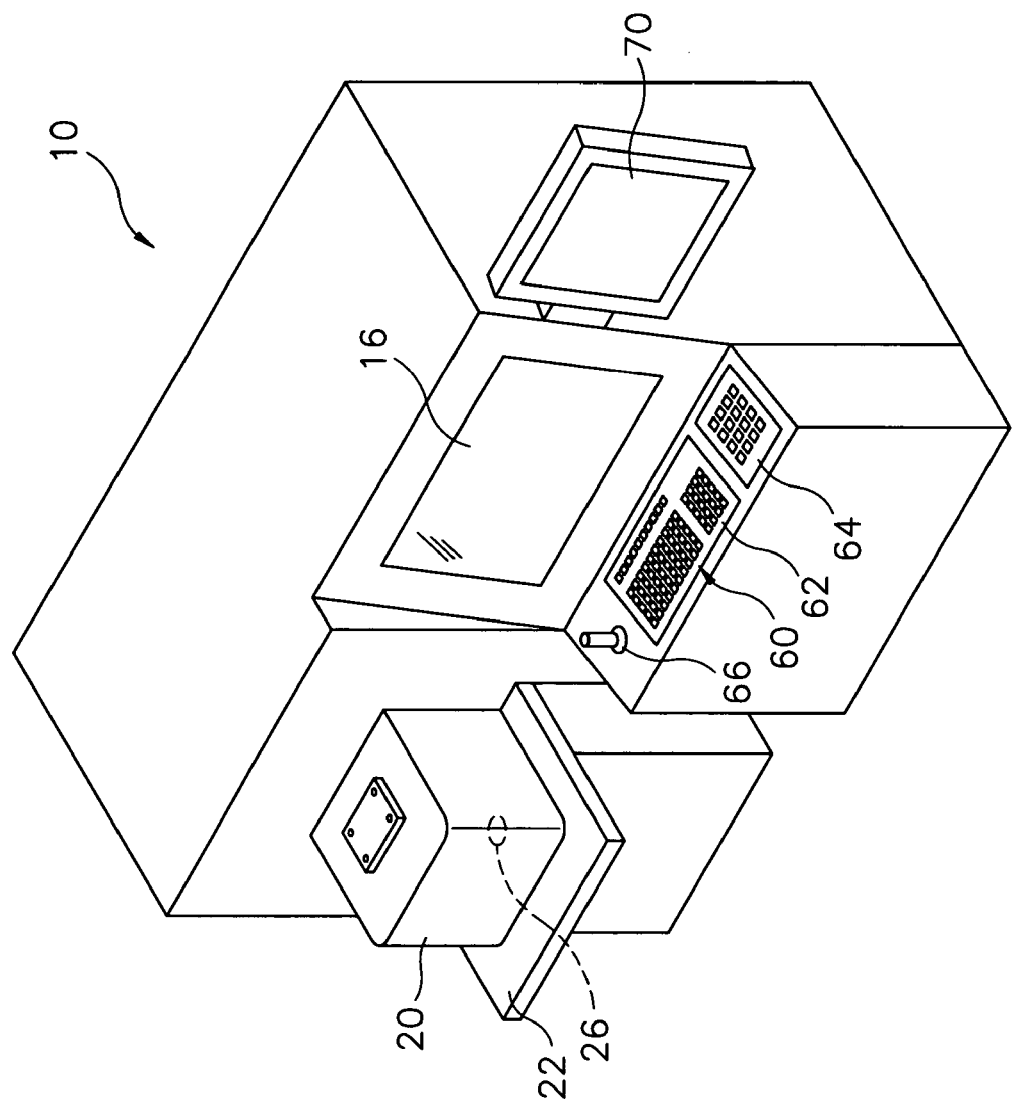
FIG. 1 illustrates a perspective view of an apparatus for inspecting a wafer according to an exemplary embodiment of the present invention.

Korean Patent Application No. 2002-72039, filed on Nov. 19, 2002, and entitled: "Apparatus for Inspecting a Wafer," is incorporated by reference herein in its entirety.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals denote like elements throughout.

Figure 2:
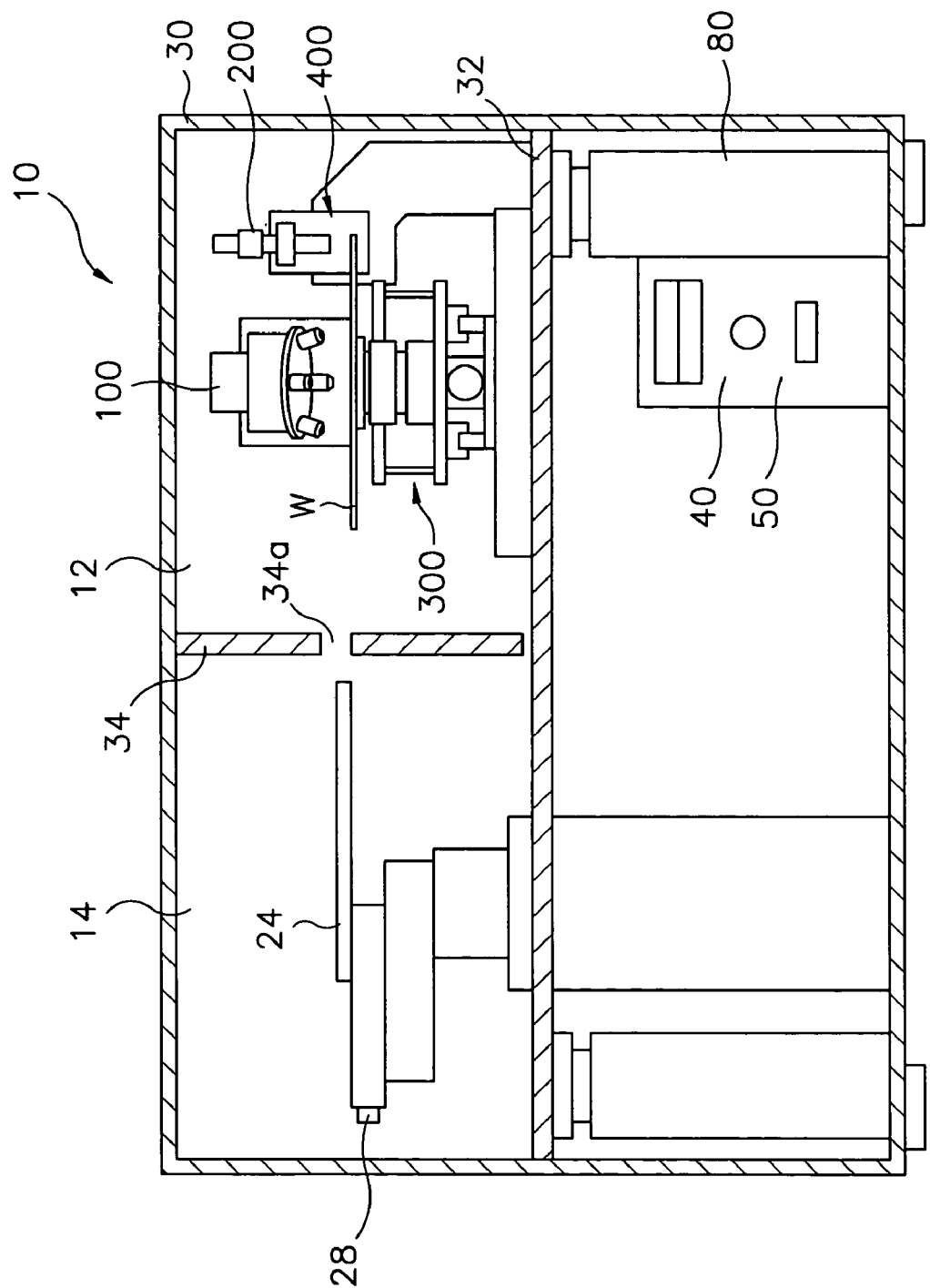
FIG. 2 illustrates a cross-sectional view of an interior of the apparatus for inspecting a wafer as shown in FIG. 1.

FIG. 1 illustrates a perspective view of an apparatus for inspecting a wafer according to an exemplary embodiment of the present invention. FIG. 2 illustrates a cross-sectional view of an interior of the apparatus for inspecting a wafer as shown in FIG. 1.

Referring to FIGS. 1 and 2, a wafer inspection apparatus 10 includes an inspection chamber 12 for performing an inspection process on a wafer W and a load chamber 14 for loading into the inspection chamber 12 the wafer W received in a container 20.

A stage 22 for supporting the container 20 is disposed at a side portion of the load chamber 14. A transfer robot 24 for transferring the wafer W between the container 20 and the inspection chamber 12 is disposed in the load chamber 14. A container sensor 26 for sensing the container 20 is installed on the stage 22. A mapping sensor 28 for sensing positions of a plurality of wafers received in the container 20 is installed at an end portion of the transfer robot 24. An example of the container sensor 26 and the mapping sensor 28 includes a light sensor having a light emitting portion and a light receiving portion.

Examples of the container 20 include an open-type conventional wafer cassette and a front opening unified pod (FOUP) for receiving wafers having a diameter of 300 mm. When a FOUP is employed as the container 20, a door opener for opening and closing a door of the FOUP may be disposed in the load chamber 14, and a driving unit is disposed in the stage 22 so that the FOUP tightly contacts the door opener.

A housing 30 defines the inspection chamber 12 and the load chamber 14. A base plate 32 is horizontally disposed in a central portion of the housing 30, and a partition wall 34 is vertically disposed between the inspection chamber 12 and the load chamber 14. As shown in the figures, the inspection chamber 12 is disposed to the right of the partition wall 34, and the load chamber 14 is disposed to the left of the partition wall 34. A first opening 34a is formed through the partition wall 34, through which the wafer W is transferred.

In the figures, the stage 22 is disposed at an outer sidewall of the load chamber 14. Alternately, the stage 22 may be disposed in the load chamber 14 on the base plate 32. When the stage 22 is disposed in the load chamber 14, a door for providing access to an interior of the container is installed in a sidewall of the load chamber 14.

The transfer robot 24 is supported on a bottom of the housing 30 and extends upwardly through the base plate 32. The transfer robot 24 loads the wafer W from the container 20 into the inspection chamber 12 and unloads the wafer W from the inspection chamber 12 into the container 20.

The inspection chamber 12 includes a handling unit 300 for handling the wafer W transferred by the transfer robot 24, a first image acquisition unit 100 for acquiring a first image, a second image acquisition unit 200 for acquiring a second image, a third image and a fourth image, and a first driving unit 400 for rotating the second image acquisition unit 200 about a peripheral portion of the wafer W supported by the handling unit 300. The first through fourth images correspond to an upper surface, a peripheral portion of the upper surface, a side surface and a lower surface of the wafer W, which is supported by the handling unit 300, respectively. The first driving unit 400 rotates the second image acquisition unit 200 about the peripheral portion of the wafer W so that the second image acquisition unit 200 can acquire the second, third and fourth images.

Figure 3:
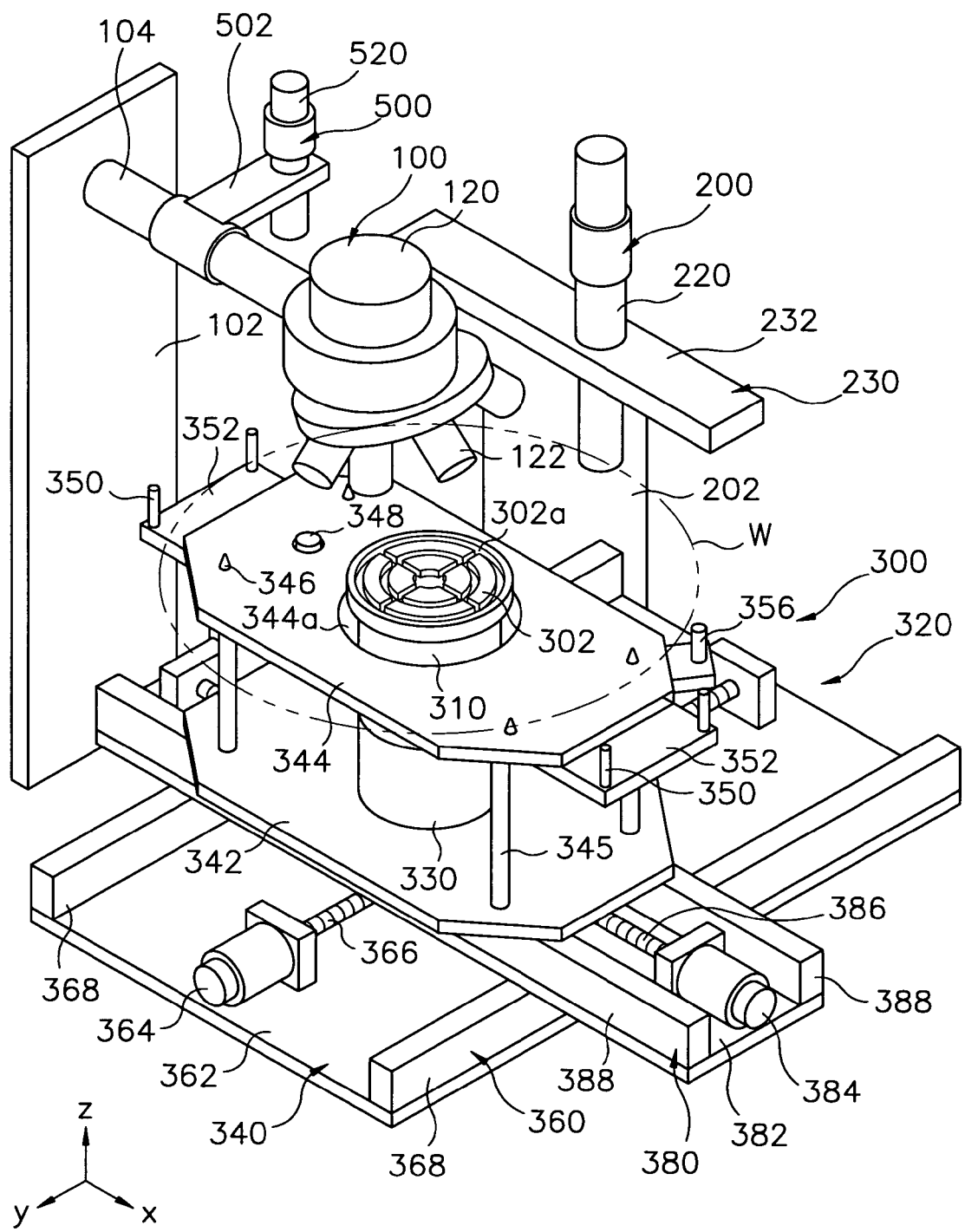
FIG. 3 illustrates a perspective view of an interior of an inspection chamber of the apparatus for inspecting a wafer as shown in FIG. 2.
Figure 4:
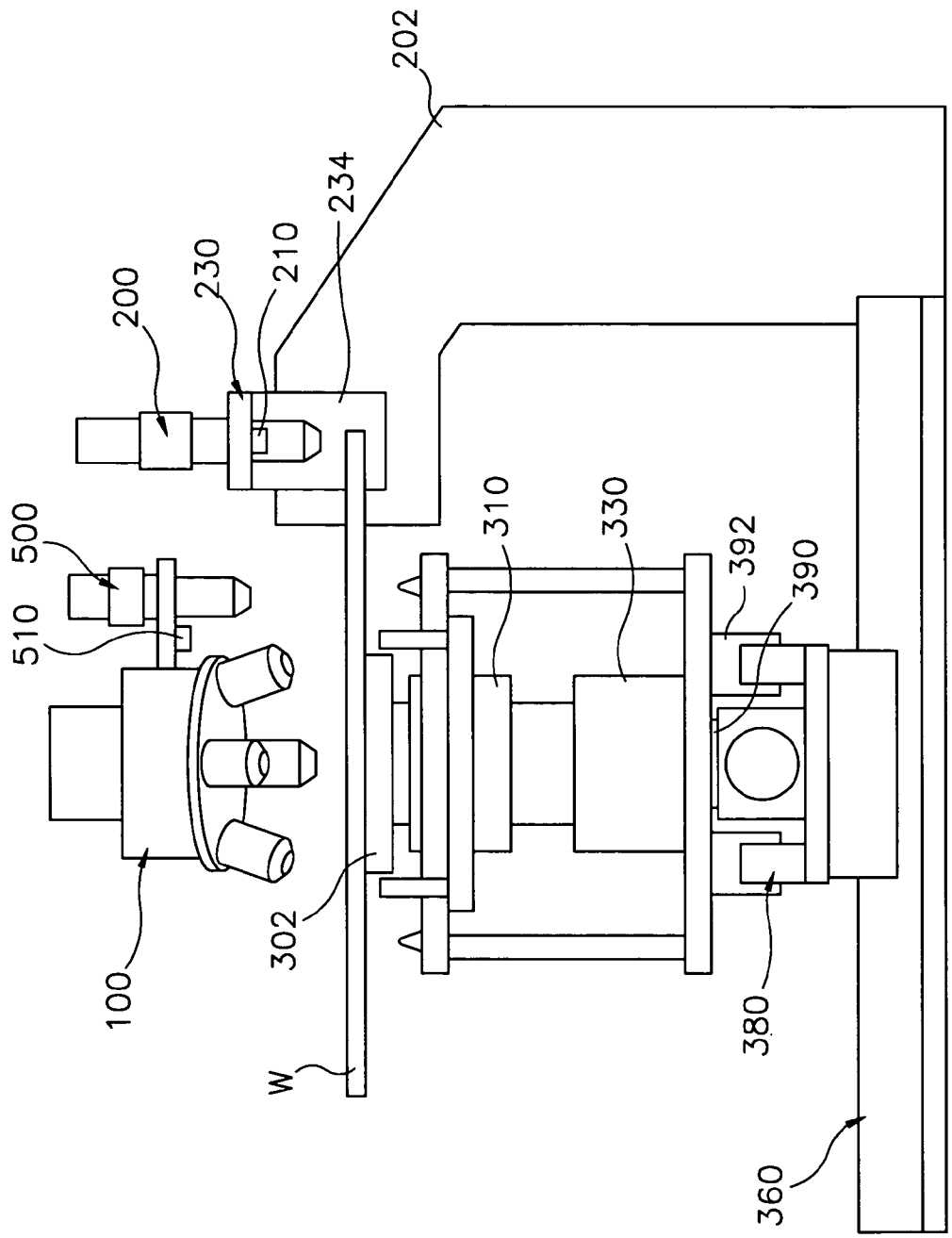
FIG. 4 illustrates a front view of the interior of the inspection chamber as shown in FIG. 3.
Figure 5:
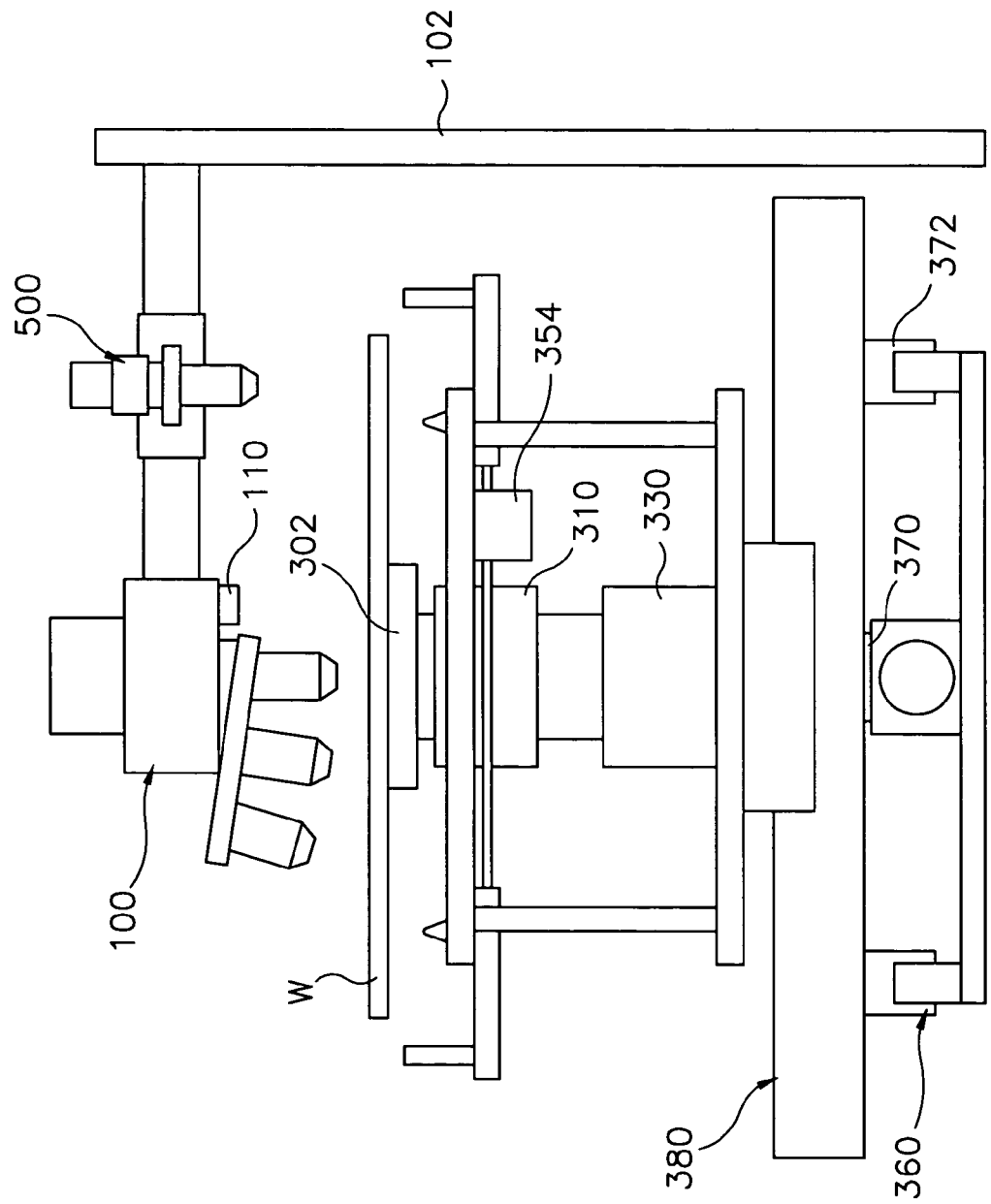
FIG. 5 illustrates a side view of a first image acquisition unit as shown in FIG. 3.
Figure 6:
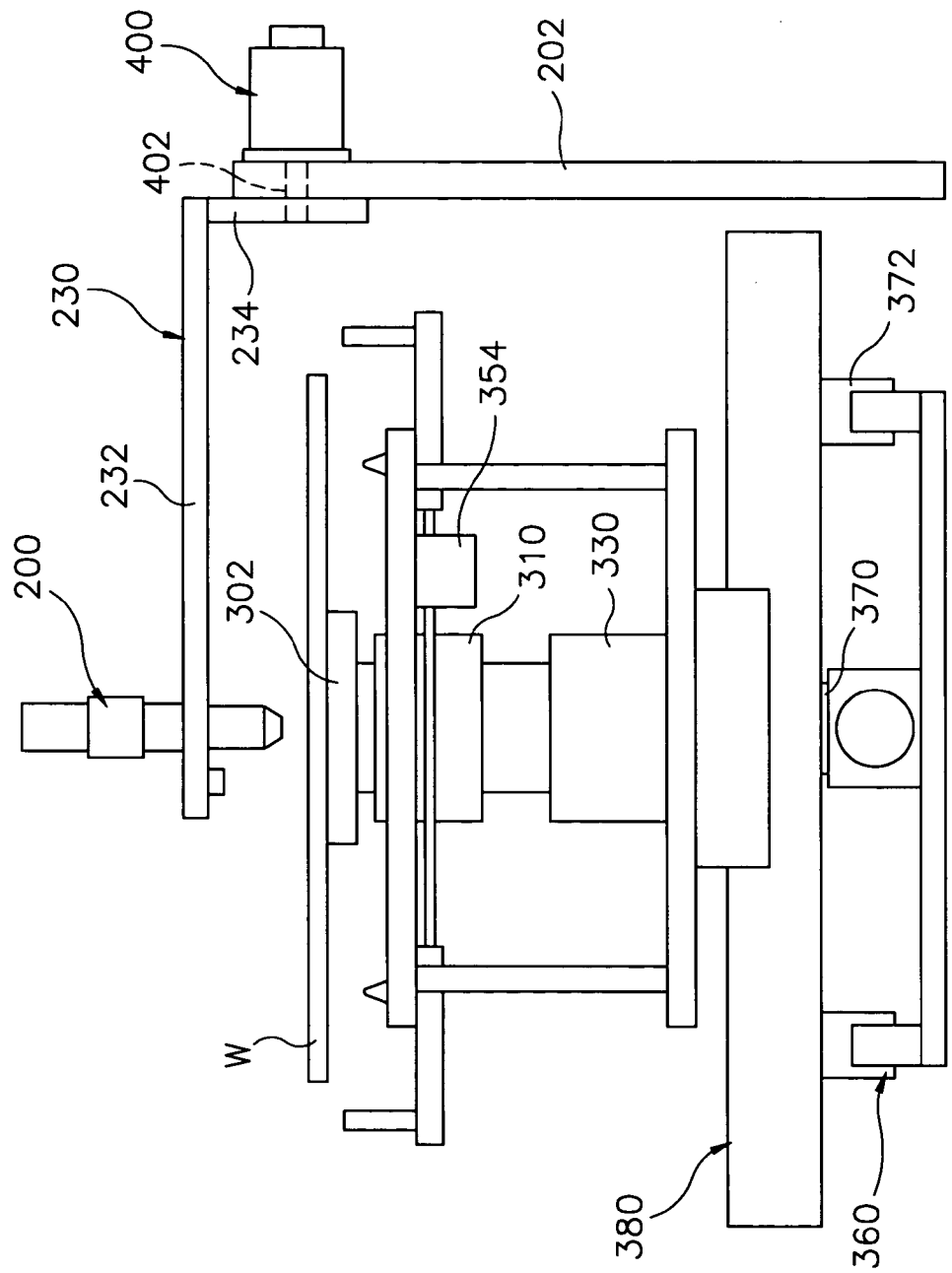
FIG. 6 illustrates a side view of a second image acquisition unit as shown in FIG. 3.

FIG. 3 illustrates a perspective view of an interior of an inspection chamber 12 of the apparatus for inspecting a wafer as shown in FIG. 2. FIG. 4 illustrates a front view of the interior of the inspection chamber 12 as shown in FIG. 3. FIG. 5 illustrates a side view of a first image acquisition unit 100 as shown in FIG. 3. FIG. 6 illustrates a side view of a second image acquisition unit 200 as shown in FIG. 3.

Referring to FIGS. 3 through 6, the handling unit 300 includes a chuck 302 for supporting the wafer W in a horizontal direction and holding the wafer W using a vacuum force, a second driving unit 310 for rotating the wafer W supported by the chuck 302, and a three-axis Cartesian coordinate robot 320 for moving the wafer W supported by the chuck in a horizontal direction and a vertical direction.

A vacuum channel 302a for holding the wafer W is formed on an upper surface of the chuck 302 and the vacuum force is supplied through the second driving unit 310. An example of the second driving unit 310 includes a step motor capable of adjusting a speed of rotation and an angle. The second driving unit 310 is connected to a lower surface of the chuck 302, and the three-axis Cartesian coordinate robot 320 is connected to a lower portion of the second driving unit 310.

The three-axis Cartesian coordinate robot 320 includes a third driving unit 330 for providing a vertical driving force and a fourth driving unit 340 for providing a horizontal driving force. The third driving unit 330 is connected to the lower portion of the second driving unit 310 and moves the chuck 302 and the second driving unit 310 vertically. The third driving unit 330 is disposed on a first plate 342 and the fourth driving unit 340 is connected to a lower surface of the first plate 342. More specifically, the fourth driving unit 340 supports the first plate 342, and the first plate 342 supports the third driving unit 330.

As shown in the figures, the third driving unit 330 includes a hydraulic cylinder or a pneumatic cylinder disposed in a z-axis direction. The fourth driving unit 340 includes a two-axis Cartesian coordinate robot of a ball screw type. The fourth driving unit 340 further includes a first robot 360 and a second robot 380 disposed at right angles with respect to each other. The first driving robot 360 is disposed on the base plate (32 of FIG. 2).

The first driving robot 360 includes a first supporting plate 362 disposed on the base plate 32, a first motor 364 for providing a driving force in an x-axis direction, a first screw 366 connected to a rotary shaft of the first motor 364 and extended in the x-axis direction, a pair of first ball guides 368 disposed parallel to the first screw 366 on both sides, a first nut 370 coupled with the first screw 366 and moving in the x-axis direction by rotation of the first screw 366, and a pair of first ball blocks 372 coupled with the pair of first ball guides 368.

The second driving robot 380 includes a second supporting plate 382, a second motor 384 for providing a driving force in a y-axis direction, a second screw 386 connected to a rotary shaft of the second motor 384 and extended in the y-axis direction, a pair of second ball guides 388 disposed parallel to the second screw 386 on both sides, a second nut 390 coupled with the second screw 386 and moving in the y-axis direction by rotation of the second screw 386, and a pair of second ball blocks 392 coupled with the pair of second ball guides 388.

The first nut 370 and the pair of first ball blocks 372 are connected to a lower surface of the second supporting plate 382. The second nut 390 and the pair of second ball blocks 392 are connected to a lower surface of the first plate 342.

The third driving unit 330 is disposed on a central portion of the first plate 342. The second driving unit 310 is connected to an upper portion of the third driving unit 330. The chuck 302 for supporting the wafer W is connected to an upper portion of the second driving unit 310. As shown in the figures, though the hydraulic cylinder or the pneumatic cylinder is employed as the third driving unit 330, a robot of the ball screw type may be employed as the third driving unit 330.

A second plate 344 having a second opening 344a is disposed above the first plate 342 and is supported by a plurality of supporting shafts 345 disposed on a peripheral portion of an upper surface of the first plate 342. The chuck 302 and the second driving unit 310 move in the vertical direction through the second opening 344a.

A plurality of supporting pins 346 is disposed on an upper surface of the second plate 344. The plurality of supporting pins 346 supports the wafer W transferred from the load chamber (14 of FIG. 2) by the transfer robot (24 of FIG. 2). The supporting pins 346 are disposed around the second opening 344a. Each supporting pin has a conical shape and a rounded upper end. When the wafer W transferred by the transfer robot 24 is supported on the supporting pins 346, the upper surface of the chuck 302 is positioned lower than the upper ends of the supporting pins 346.

A wafer sensor 348 for sensing when the wafer W is placed on the supporting pins 346 is installed on the upper surface of the second plate 344. An example of the wafer sensor 348 can include a light sensor having a light emitting portion and a light receiving portion. In order to sense a wafer, the wafer sensor 348 directs light onto a lower surface of the wafer W and detects light reflected from the lower surface of the wafer W.

A plurality of alignment pins 350 is installed in both side portions of the second plate 344. A pair of alignment plates 352 is movably disposed on a lower surface of the second plate 344 in the horizontal direction, and the plurality of alignment pins 350 is upwardly disposed on the pair of alignment plates 352. A fifth driving unit 354 is disposed on the lower surface of the second plate 344 and is operatively connected to the pair of the alignment plates 352. The plurality of alignment pins 350 simultaneously moves towards the chuck 302 by means of operation of the fifth driving unit 354 and is closely contacted with a side surface of the wafer W. Then, a center of the wafer W can be aligned with a central axis of the chuck 302. The wafer W aligned by the plurality of alignment pins 350 is held on the upper surface of the chuck 302 by the vacuum force.

A notch sensor 356 for sensing a notch portion of the wafer W is installed on another portion of the second plate 344. An example of the notch sensor 356 can include a light sensor. The second driving unit 310 rotates the wafer W so the notch sensor 356 can sense the notch portion of the wafer W.

In operation, the first image acquisition unit 100 acquires the first image corresponding to the upper surface of the wafer W aligned by the plurality of alignment pins 350 and the notch sensor 356. A first supporting bracket 102 extends upwardly from the base plate 32 in order to support the first image acquisition unit 100. The first supporting bracket 102 is disposed on a first portion of the base plate 32 adjacent the handling unit 300. The first image acquisition unit 100, which is connected to an upper portion of the first supporting bracket 102, is placed above the wafer W supported the handling unit 300.

The first image acquisition unit 100 includes a first light source 110 for directing light onto the upper surface of the wafer W and a first charge coupled device (CCD) camera 120 for acquiring the first image of the wafer W using light reflected from the upper surface of the wafer W. The first CCD camera 120 includes a plurality of object lenses 122 having various magnifications and a CCD memory (not shown) for storing the first image. The first image acquisition unit 100 is connected to the upper portion of the first supporting bracket 102 by means of a first horizontal arm 104 extended from the upper portion of the first supporting bracket 102.

The handling unit 300 moves the wafer W in the x-axis direction and the y-axis direction or rotates the wafer W so the first image acquisition unit 100 can acquire the first image corresponding to the entire upper surface of the wafer W.

The second image acquisition unit 200 acquires the second, third, and fourth images corresponding to the peripheral portion of the upper surface, the side surface and the lower surface of the wafer W, respectively. A second supporting bracket 202 extends upwardly from the base plate 32 to support the second image acquisition unit 200. The second supporting bracket 202 is disposed on a second portion of the base plate 32 adjacent the handling unit 300. The first driving unit 400 and the second image acquisition unit 200 are connected to an upper portion of the second supporting bracket 202. The second image acquisition unit 200 includes a second light source 210 for directing light onto the peripheral portion of the upper surface, the side surface and the lower surface of the wafer W, respectively, and a second charge coupled device (CCD) camera 220 for acquiring the second, third and fourth images of the wafer W.

A supporting arm 230 for supporting the second image acquisition unit 200 is extended from a first side surface of the second supporting bracket 202 adjacent to the handling unit 300. The first driving unit 400 for rotating the second image acquisition unit 200 is connected to a second surface of the second supporting bracket 202. An example of the first driving unit 400 can include step motor capable of adjusting a speed of rotation and an angle. A rotary shaft 402 of the first driving unit 400 is connected to the supporting arm 230 passing through the second supporting bracket 202.

The second image acquisition unit 200, which is supported by the supporting arm 230, is positioned neared the peripheral portion of the wafer W. The first driving unit 400 rotates the supporting arm 230 so that the second image acquisition unit 200 is rotated about the peripheral portion of the wafer W and acquires the second, third, and fourth images.

While the second image acquisition unit 200 is supported near the peripheral portion of the upper surface of the wafer W, the handling unit 300 rotates the wafer W so the second image acquisition unit 200 can acquire the second image. Furthermore, while the second image acquisition unit 200 is supported near the side and lower surfaces of the wafer W, the handling unit 300 rotates the wafer W so the second image acquisition unit 200 can acquire the third and fourth images, respectively.

The supporting arm 230 includes a second horizontal arm 232 disposed parallel to the rotary shaft 402 of the first driving unit 400 and a connecting arm 234 for connecting the rotary shaft 402 of the first driving unit 400 and the second horizontal arm 232.

A third image acquisition unit 500 is supported by a third horizontal arm 502 and acquires an identification pattern image of the wafer W supported by the handling unit 300. The third horizontal arm 502 extends from the first horizontal arm 104 in the horizontal direction. The third image acquisition unit 500 includes a third light source 510 and a third CCD camera 520.

Referring back to FIGS. 1 and 2, an image processing unit 40 and a central processing unit 50 are disposed under the base plate 32. The image processing unit 40 is connected to the first, second and third image acquisition units 100, 200 and 500, respectively, and the central processing unit 50 controls operations of these elements of the wafer inspection apparatus 10 and manages an inspection result data of the wafer W produced by the image processing unit 40 and various image data of the wafer W.

A transparent window 16 is installed in a sidewall of the inspection chamber 12 so an operator can observe an interior of the inspection chamber 12. An operating unit 60 for operating the image processing unit 40 and the central processing unit 50 is disposed under the transparent window 16. The operating unit 60 can include a keyboard 62, a touch screen 64 and a joystick 66. The operator can directly control the handling unit 300 and the first driving unit 400 using the joystick 66. Furthermore, the operator can edit the various images of the wafer W using the keyboard 62 and control the magnifications of the first and second image acquisition units 100 and 200, respectively.

The image processing unit 40 detects surface defects of the wafer W by comparing various images sent from the first and second image acquisition unit 100 and 200 with reference images stored in the central processing unit 50. Furthermore, the image processing unit 40 is able to perform editing functions, such as zoom-in, zoom-out, conversion, and the like. A display unit 70 connected to the image processing unit 40 displays the various images of the wafer W sent from the image processing unit 40 so the operator can observe the images with the naked eye.

A plurality of vibration control units 80 is connected to a lower portion of the base plate 32 so that a shock or a vibration from the outside does not affect the elements on the base plate 32. The vibration control units 80 are connected to peripheral portions of the lower portion of the base plate 32 and support the base plate 32 in the housing 30.

Figure 7:
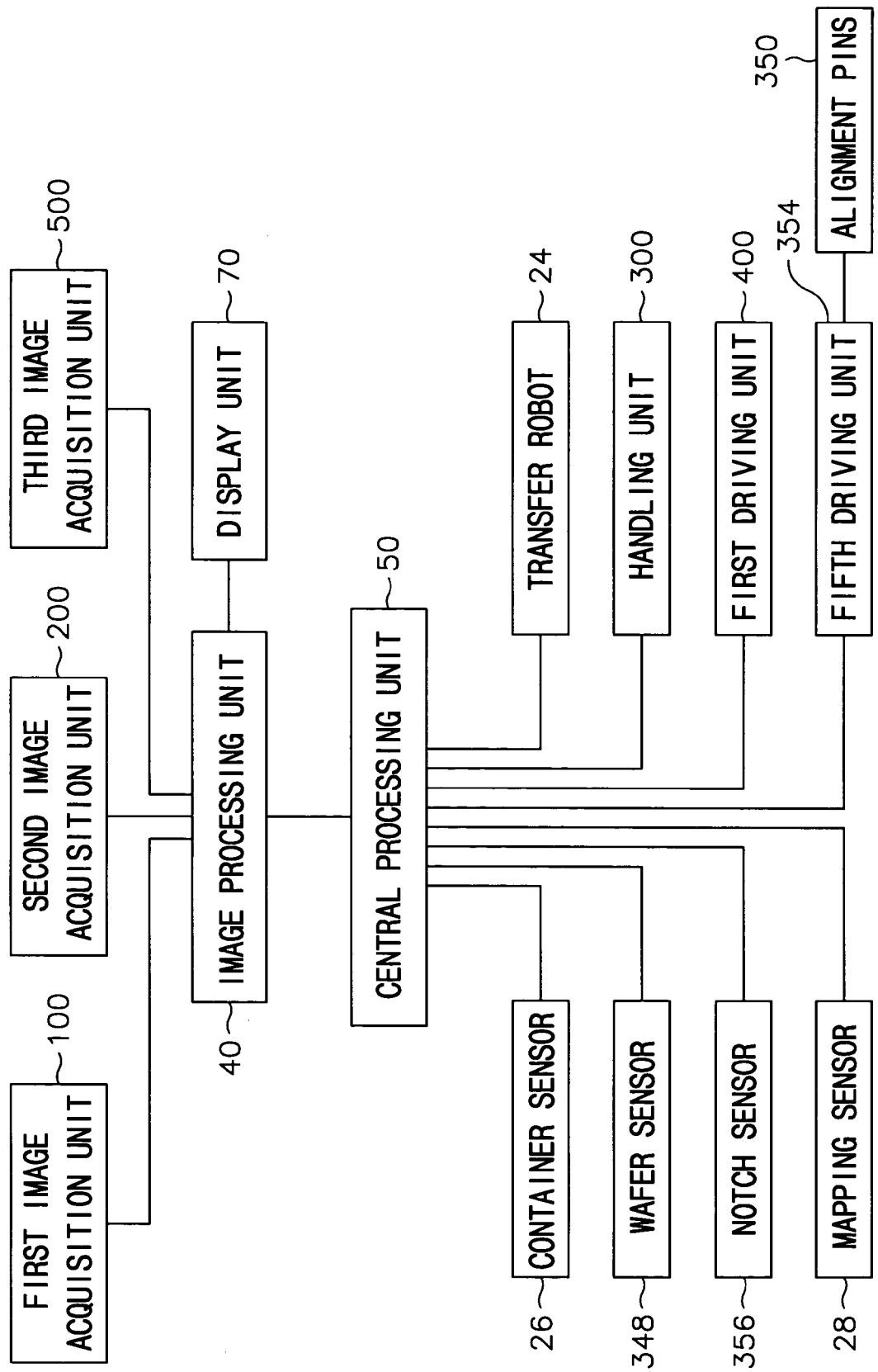
FIG. 7 is a block diagram illustrating the apparatus for inspecting a wafer as shown in FIGS. 1 and 2.

FIG. 7 is a block diagram illustrating the apparatus for inspecting a wafer as shown in FIGS. 1 and 2.

Hereinafter, a wafer inspection process using the wafer inspection apparatus 10 will be described in detail with reference to FIGS. 1 through 7.

When the container 20 for receiving the plurality of wafers is placed on the stage 22, the container sensor 26 installed in the stage 22 sends a signal indicating the presence of the container 20 to the central processing unit 50.

The mapping sensor 28 installed in the transfer robot 24 detects locations of the plurality of wafers received in the container 20 and sends mapping data of the plurality of wafers to the central processing unit 50.

The transfer robot 24 transfers a wafer W selected from the plurality of wafers from the container 20 into the inspection chamber 12 through the first opening 34a of the partition wall 34. The wafer W transferred by the transfer robot 24 is placed on the plurality of supporting pins 346, and the transfer robot 24 returns into the load chamber 14.

The transfer robot 24 selects the wafer W from among the plurality of wafers according to a control signal from the central processing unit 50.

The wafer sensor 348 installed on the second plate 344 senses the wafer W and sends a wafer sense signal to the central processing unit 50. Next, the central processing unit 50 operates the handling unit 300.

The central processing unit 50 successively generates a first and a second alignment signal to align the wafer W. The third driving unit 330 raises the chuck 302 according to the first alignment signal, and then the chuck 302 supports the wafer W. The plurality of alignment pins 350 simultaneously moves toward the chuck 302 to align the center of the wafer W with a central axis of the chuck 302. The chuck 302 holds the wafer W using the vacuum force after the plurality of alignment pins 350 returns to an initial position. The second driving unit 310 rotates the wafer W held on the chuck 302, and the notch sensor 356 detects the notch portion of the wafer W.

The third image acquisition unit 500 acquires the identification pattern image of the aligned wafer W and sends the identification pattern image to the image processing unit 40. The display unit 70 then displays the identification pattern image. The image processing unit 40 determines an identification number of the wafer W by comparing the identification pattern image with a first reference image stored in the central processing unit 50. Subsequently, the identification number is stored in the central processing unit 50.

The central processing unit 50 operates the fourth driving unit 340 to move the wafer W into a first position for acquiring the first image. While the first image acquisition unit 100 acquires the first image, the fourth driving unit 340 can rotate or move the wafer W in a zigzag direction as needed. The acquired first image is sent to the image processing unit 40 and is displayed through the display unit 70. In addition, the acquired first image is stored in the central processing unit 50. The image processing unit 40 detects the defects of the wafer W, such as a defect of a pattern formed on the wafer W or particles remaining on the wafer, by comparing the acquired first image with a second reference image stored in the central processing unit 50. An inspection result data produced by the image processing unit 40 is stored in and managed by the central processing unit 50.

The central processing unit 50 operates the fourth driving unit 340 to move the wafer W into a second position for acquiring the second, third and fourth images. The second image acquisition unit 200 is placed near the peripheral portion of the wafer W, and the first driving unit 400 adjusts the angle of rotation of the second image acquisition unit 200 according to the images to be acquired as shown in FIGS. 8A through 8E.

FIGS. 8A through 8E illustrate front views showing stages in an operation of the second image acquisition unit as shown in FIG. 3.

Figure 8A:
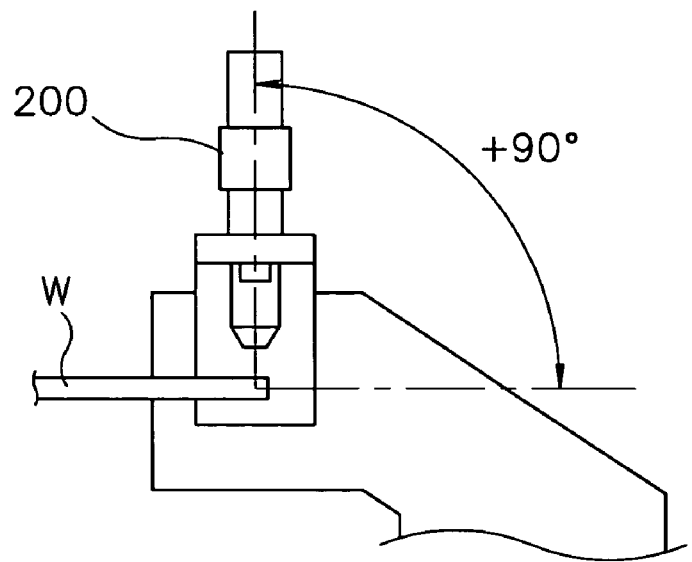
FIGS. 8A through 8E illustrate front views showing stages in an operation of the second image acquisition unit as shown in FIG. 3.

As shown in FIG. 8A, when the second image acquisition unit 200 has a rotation angle of +90° relative to the wafer W on the chuck 302, the second image acquisition unit 200 acquires the second image corresponding to the peripheral portion of the upper surface of the wafer W. During acquisition of the second image, the second driving unit 310 rotates the wafer W at suitable rotation speed.

Figure 8B:
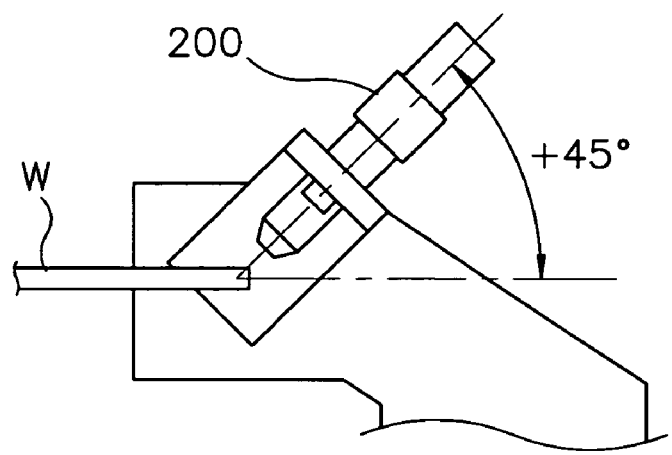
Figure 8C:
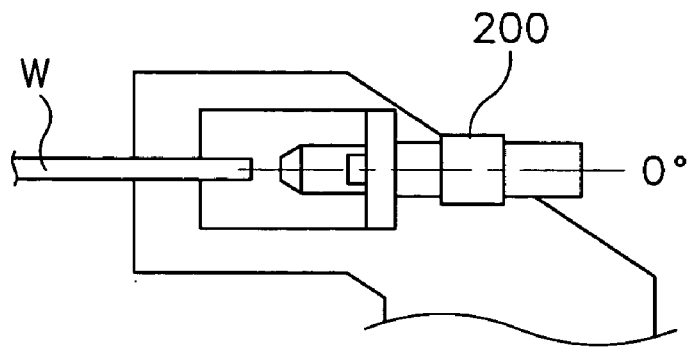
Figure 8D:
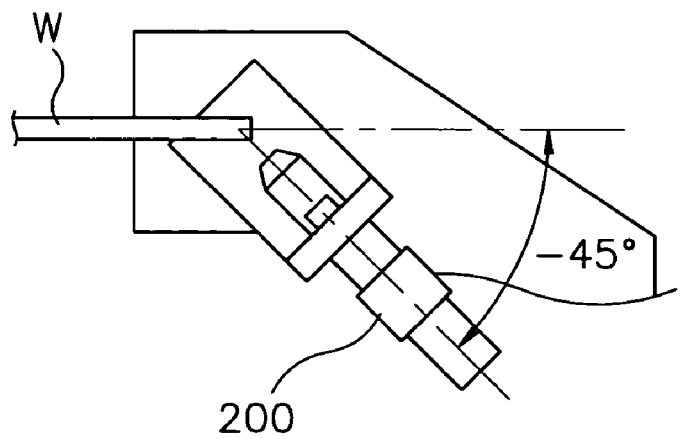

As shown in FIGS. 8B through 8D, the first driving unit 400 adjusts the angle of rotation of the second image acquisition unit 200, such as to +45°, 0° and −45° relative to the wafer W, so that the second image acquisition unit 200 is able to acquire the third image corresponding to the entire side surface of the wafer W. During acquisition of the third image, the second driving unit 310 rotates the wafer W at suitable rotation speed.

Figure 8E:
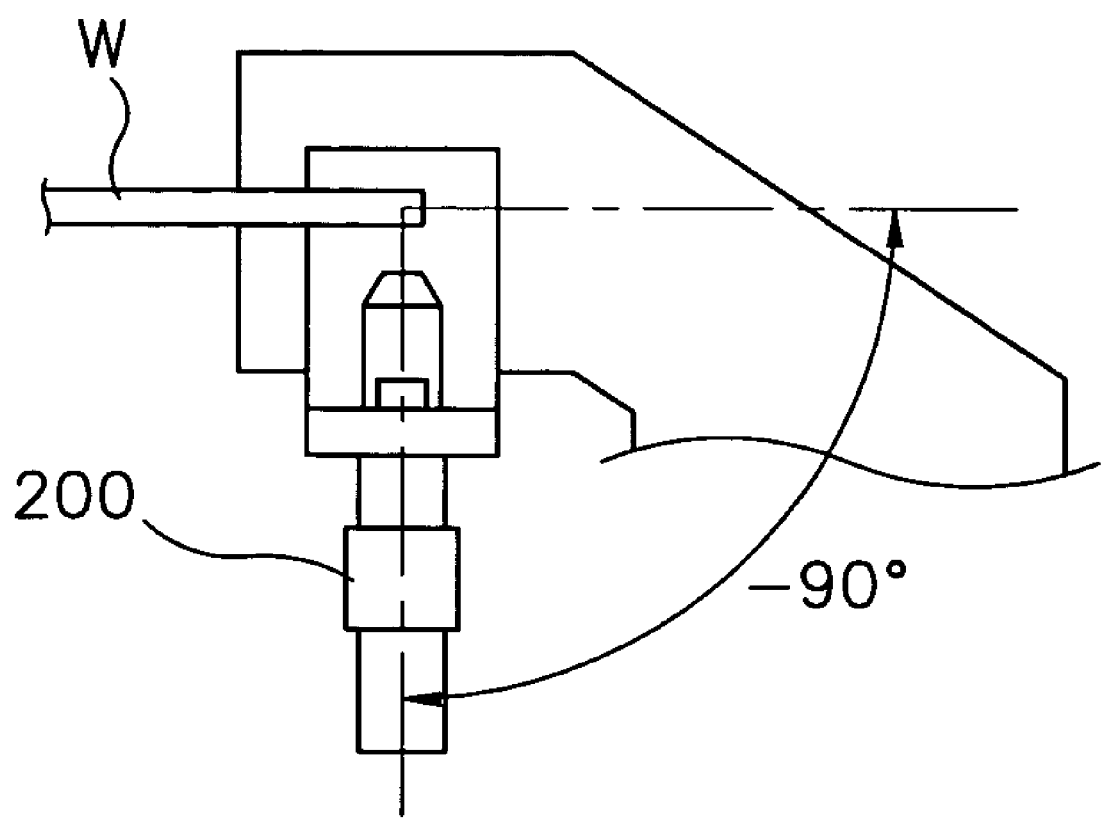

As shown in FIG. 8E, when the second image acquisition unit 200 has a rotation angle of −90° relative to the wafer W on the chuck 302, the second image acquisition unit 200 acquires the fourth image corresponding to the lower surface of the wafer W. During acquisition of the fourth image, the second driving unit 310 rotates the wafer W at suitable rotation speed, and the fourth driving unit 340 moves the wafer W horizontally as needed.

The image processing unit 40 processes the second, third, and fourth images sent from the second image acquisition unit 200 in a similar method to the first image. The image processing unit 40 can inspect from the second image whether an edge bead removal (EBR) process or an edge exposure of wafer (EEW) process has been performed normally. The EBR process or the EEW process is a process for removing a peripheral portion of a photoresist film formed on the wafer. Furthermore, the image processing unit 40 is able to inspect for a contamination of the peripheral portion of the wafer W, a damage, such as scratch and being broken, particles, and the like using the second, third, and fourth images.

The central processing unit 50 controls the angle of rotation of the second image acquisition unit 200, the speed of rotation of the wafer W, an interval between the second image acquisition unit 200 and the peripheral portion of the wafer W, and the like, so that the second image acquisition unit 200 can acquire the various images. Furthermore, the central processing unit 50 stores and manages an inspection result data on the peripheral portion of the wafer W.

When the wafer inspection process is completed, the vacuum force supplied in the vacuum channel 302a is removed, the third driving unit 330 lowers the chuck 302, and the plurality of supporting pins 346 supports the wafer W. Subsequently, the transfer robot 24 returns the wafer W from the inspection chamber 12 to the container 20.

Alternately, though the second image corresponding to the peripheral portion of the upper surface of the wafer is acquired by the second image acquisition unit 200, the second image may be acquired by the first image acquisition unit 100. In addition, the inspection processes on the upper, side and lower surfaces of the wafer may be individually performed.

According to an embodiment of the present invention, the wafer inspection apparatus is able to perform the inspection process on the upper, side and lower surfaces of the wafer, thereby improving an efficiency of the wafer inspection process and reducing the time required for the wafer inspection process. Furthermore, an embodiment of the present invention reduces the cost associated with equipment investment and repair work and improves the productivity of the semiconductor device. Further still, the handling unit supports the wafer during the inspection process, thereby preventing damage to the wafer.

Exemplary embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. An apparatus for inspecting a wafer, comprising:
a handling unit for supporting, rotating and moving the wafer in horizontal and vertical directions;
a first image acquisition unit for acquiring a first image corresponding to an upper surface of the wafer supported by the handling unit;
a second image acquisition unit for acquiring a second image, a third image and a fourth image corresponding to a peripheral portion of the upper surface, a side surface and a lower surface of the wafer supported by the handling unit, respectively;
a first driving unit for rotating the second image acquisition unit about a peripheral portion of the wafer supported by the handling unit in order to acquiring the second, third and fourth images; and
an image processing unit for inspecting defects of the wafer supported by the handling unit from the first to fourth images.

2. The apparatus for inspecting a wafer as claimed in claim 1, wherein the first driving unit is a step motor.

3. The apparatus for inspecting a wafer as claimed in claim 1, wherein the handling unit comprises:
a chuck for supporting the wafer;
a second driving unit, connected to the chuck, for rotating the chuck and the wafer;
a third driving unit, connected to the second driving unit, for moving the chuck and the second driving unit vertically;
a first plate for supporting the third driving unit; and
a fourth driving unit, connected to a lower surface of the first plate, for moving the chuck, the second driving unit and the third driving unit horizontally.

4. The apparatus for inspecting a wafer as claimed in claim 3, wherein the second driving unit is a step motor.

5. The apparatus for inspecting a wafer as claimed in claim 3, wherein the third driving unit comprises either a hydraulic cylinder or a pneumatic cylinder.

6. The apparatus for inspecting a wafer as claimed in claim 3, wherein the third driving unit comprises a ball screw type robot.

7. The apparatus for inspecting a wafer as claimed in claim 3, wherein the fourth driving unit comprises a two-axis Cartesian coordinate robot of a ball screw type.

8. The apparatus for inspecting a wafer as claimed in claim 3, wherein the fourth driving unit comprises a first driving robot and a second driving robot.

9. The apparatus for inspecting a wafer as claimed in claim 8, wherein the first driving robot comprises:
a first motor for providing a driving force in an x-axis direction;
a first screw connected to a rotary shaft of the first motor and extended in the x-axis direction;
a pair of first ball guides disposed parallel to the first screw on both sides;
a first nut coupled with the first screw and moving in the x-axis direction by rotation of the first screw; and
a pair of first ball blocks coupled with the pair of first ball guides.

10. The apparatus for inspecting a wafer as claimed in claim 8, wherein the second driving robot comprises:
a second motor for providing a driving force in a y-axis direction;
a second screw connected to a rotary shaft of the second motor and extended in the y-axis direction;
a pair of second ball guides disposed parallel to the second screw on both sides;
a second nut coupled with the second screw and moving in the y-axis direction by rotation of the second screw; and
a pair of second ball blocks coupled with the pair of second ball guides.

11. The apparatus for inspecting a wafer as claimed in claim 3, wherein the handling unit further comprises:
a second plate having an opening, the chuck and the second driving unit moving in the vertical direction through the opening;
a plurality of supporting shafts extending from an upper surface of the plate in the vertical direction in order to support the second plate; and
a plurality of supporting pins disposed on an upper surface of the second plate for supporting the wafer while the chuck is placed at a position lower than those of the plurality of supporting pins.

12. The apparatus for inspecting a wafer as claimed in claim 11, wherein each of the plurality of supporting pin has a conical shape and a rounded upper end.

13. The apparatus for inspecting a wafer as claimed in claim 11, further comprising a plurality of alignment pins, movably installed in the horizontal direction at peripheral portions of the second plate, for simultaneously moving the wafer supported by the chuck towards the chuck to align a center of the wafer with a central axis of the chuck.

14. The apparatus for inspecting a wafer as claimed in claim 13, further comprising:
a pair of alignment plates movably disposed on a lower surface of the second plate in the horizontal direction; and
a fifth driving unit disposed on the lower surface of the second plate and operatively connected to the pair of the alignment plates for moving the plurality of alignment pins.

15. The apparatus for inspecting a wafer as claimed in claim 11, further comprising a wafer sensor for sensing the wafer supported by the plurality of supporting pins.

16. The apparatus for inspecting a wafer as claimed in claim 15, wherein the wafer sensor comprises a light sensor having a light emitting portion and a light receiving portion.

17. The apparatus for inspecting a wafer as claimed in claim 1, wherein the first and second image acquisition units comprise:
a light source for illuminating the wafer supported by the handling unit; and
a CCD (charge coupled device) camera for acquiring the images of wafer supported by the handling unit.

18. The apparatus for inspecting a wafer as claimed in claim 1, wherein the first driving unit comprises:
a motor for providing a driving force to rotate the second image acquisition unit and a supporting arm connected to the motor to support the second image acquisition unit so that the second image acquisition unit is placed near the peripheral portion of the wafer supported by the handling unit.

19. The apparatus for inspecting a wafer as claimed in claim 18, wherein the supporting arm comprises:
a horizontal arm disposed parallel to a rotary shaft of the motor to support the second image acquisition unit and a connecting arm for connecting the horizontal arm and the rotary shaft of the motor.

20. The apparatus for inspecting a wafer as claimed in claim 1, further comprising:
an inspection chamber for performing a process for inspecting defects of the wafer supported by handling unit;

a load chamber connected to the inspection chamber for loading and unloading the wafer;

a transfer robot disposed in the load chamber for transferring the wafer between a container for receiving a plurality of wafers and the inspection chamber; and a stage connected to the load chamber for supporting the container.

21. The apparatus for inspecting a wafer as claimed in claim 20, further comprising:

a mapping sensor electrically connected to the transfer robot for sensing positions of the plurality of wafers received in the container.

22. The apparatus for inspecting a wafer as claimed in claim 21, wherein the mapping sensor comprises a light emitting portion and a light receiving portion.

23. The apparatus for inspecting a wafer as claimed in claim 20, further comprising:

a container sensor installed on the stage for sensing the container.

24. The apparatus for inspecting a wafer as claimed in claim 23, wherein the container sensor comprises a light emitting portion and a light receiving portion.

25. The apparatus for inspecting a wafer as claimed in claim 1, further comprising:

a notch sensor for sensing a notch portion of the wafer supported by the handling unit and a third image acquisition unit for acquiring an identification image corresponding to an identification pattern of the wafer supported by the handling unit.

26. The apparatus for inspecting a wafer as claimed in claim 25, wherein the notch sensor is a light sensor.

27. The apparatus for inspecting a wafer as claimed in claim 25, wherein the third image acquisition unit comprises:

a light source; and a CCD camera.

28. The apparatus for inspecting a wafer as claimed in claim 25, further comprising:

a display unit connected to the image processing unit for displaying the images.

29. The apparatus for inspecting a wafer as claimed in claim 1, further comprising:

a base plate for supporting the handling unit, the first image acquisition unit, the second image acquisition and the driving unit; and a vibration control unit for supporting the base plate and for controlling a vibration.

30. The apparatus for inspecting a wafer as claimed in claim 1, further comprising:

a central processing unit for controlling operations of the handling unit and the first image acquisition unit in order to acquire the first image, for controlling operations of the handling unit, the second image acquisition unit and the driving unit, and for managing inspection result data of the wafer produced by the image processing unit.

31. An apparatus for inspecting a wafer, comprising:

a chuck for supporting a wafer and for holding the wafer using a vacuum force;

a first driving unit connected to a lower surface of the chuck for rotating the wafer held by the chuck;

a three-axis Cartesian coordinate robot for moving the wafer held by the chuck in horizontal and vertical directions;

a first image acquisition unit for acquiring a first image corresponding to an upper surface of the wafer held by the chuck;

a second image acquisition unit for acquiring a second image, a third image and a fourth image corresponding to a peripheral portion of the upper surface, a side surface and a lower surface of the wafer held by the chuck, respectively;

a second driving unit for rotating the second image acquisition unit about a peripheral portion of the wafer held by the chuck in order to acquiring the second, third and fourth images;

a supporting arm for supporting the second image acquisition unit and for connecting the second image acquisition unit and the second driving unit so that the second image acquisition unit is placed near the peripheral portion of the wafer held by the chuck; and an image processing unit for inspecting defects of the wafer held by the chuck from the first to fourth images.

32. The apparatus for inspecting a wafer as claimed in claim 31, wherein the three-axis Cartesian coordinate robot comprises:

a third driving unit connected with the first driving unit for moving the wafer held by the chuck in the vertical direction;

a first plate for supporting the third driving unit;

a two-axis Cartesian coordinate robot for supporting the first plate and for moving the wafer by the chuck in the horizontal direction;

a second plate disposed over the first plate and having a opening so that the first driving unit moves through the opening;

a plurality of supporting shafts for supporting the second plate, the plurality of supporting shafts extending from a upper surface of the first plate in the vertical direction; and a plurality of alignment pins, movably installed in the horizontal direction at peripheral portions of the second plate, for simultaneously moving the wafer supported by the chuck towards the chuck in order to align a center of the wafer with a central axis of the chuck.

33. The apparatus for inspecting a wafer as claimed in claim 31, wherein the supporting arm comprises:

a horizontal arm disposed in parallel with a rotary shaft of the second driving unit for supporting the second image acquisition unit and a connecting arm for connecting the horizontal arm and the rotary shaft of the second driving unit.

* * * * *